United States Patent [19]

Fujii et al.

[11] Patent Number: 5,917,876
[45] Date of Patent: Jun. 29, 1999

[54] COMPUTED TOMOGRAPHY SCANNER

[75] Inventors: Masashi Fujii; Kiichiro Uyama, both of Tokyo, Japan

[73] Assignee: Kabushiki Kaisha Toshiba, Kawasaki, Japan

[21] Appl. No.: 08/959,978

[22] Filed: Oct. 29, 1997

Related U.S. Application Data

[63] Continuation of application No. 08/684,198, Jul. 19, 1996, abandoned, which is a continuation of application No. 08/335,969, Nov. 4, 1994, abandoned.

[30] Foreign Application Priority Data

Nov. 5, 1993 [JP] Japan ................................. 5-276275

[51] Int. Cl.$^6$ .............................................. G01N 23/00
[52] U.S. Cl. .............................................. 378/4; 378/59
[58] Field of Search .................................. 378/4, 59

[56] References Cited

U.S. PATENT DOCUMENTS

| | | | |
|---|---|---|---|
| 4,084,094 | 4/1978 | Froggatt | 378/13 |
| 4,134,020 | 1/1979 | Zonneveld | 378/13 |
| 4,200,799 | 4/1980 | Saito | 378/13 |
| 4,606,062 | 8/1986 | Saito | 378/13 |
| 4,969,165 | 11/1990 | Bernardi et al. | 378/13 |
| 5,119,408 | 6/1992 | Little et al. | |
| 5,485,492 | 1/1996 | Pelc | 378/5 |

FOREIGN PATENT DOCUMENTS

| | | |
|---|---|---|
| 60-242348 | 12/1985 | Japan . |
| 2-195237 | 8/1990 | Japan . |
| 2-50508 | 11/1990 | Japan . |
| 6-218844 | 8/1994 | Japan . |
| 2 232 332 | 12/1990 | United Kingdom . |

OTHER PUBLICATIONS

Patent Abstracts of Japan, vol. 10, No. 111 (P–451)(2168), Apr. 25, 1986, JP–A–60 242348, Dec. 2, 1985.
Patent Abstracts of Japan, vol. 9, No. 210 (P–383)(1933), Aug. 28, 1985, JP–A–60 73441, Apr. 25, 1985.
Toshiba Review, No. 160, Summer 1987, pp. 13–17, Yoshinori Tanimoto, et al., "X–Ray CT Scanner for Heavy and Valuable Components".
NDT International, vol. 23, No. 5, pp. 255–261, Oct. 1990, P. Reimers, et al., "Region–of–Interest (ROI) Mode in Industrial X–Ray Computed Tomography".
Acta Electronica, vol. 22, No. 1. pp. 51–62, 1979, G. Kowalski, et al., "New Means for Picture Formation in Computer Tomography".
SPIE Recent and Future Developments in Medical Imaging II, vol. 206, pp. 98–102, 1979, O. Nalcioglu, et al., "Region of–Interest X–Ray Tomography (ROIT)".

*Primary Examiner*—Craig E. Church
*Attorney, Agent, or Firm*—Oblon, Spivak, McClelland, Maier & Neustadt, P.C.

[57] ABSTRACT

A computed tomography scanner for obtaining a tomographic image of a subject to be examined including a radiation emitting device for emitting radiation in a shape of a fan beam to the subject, a radiation detecting device for detecting the radiation that has passed through the subject to obtain detection data with respect to a tomographic plane of the subject. The radiation emitting device and the radiation detecting device determines a scanning area constituting a data collection region in a radiation plane of the fan beam. The subject has external dimensions exceeding the scanning area. The computed tomography scanner further includes a scanning device for relatively moving the subject, the radiation emitting device and the radiation detecting device in a condition that the radiation plane and the tomographic plane are on a same plane and a device for obtaining the tomographic image of a part of the subject corresponding to the scanning area from the detection data obtained by the radiation detecting device.

10 Claims, 8 Drawing Sheets

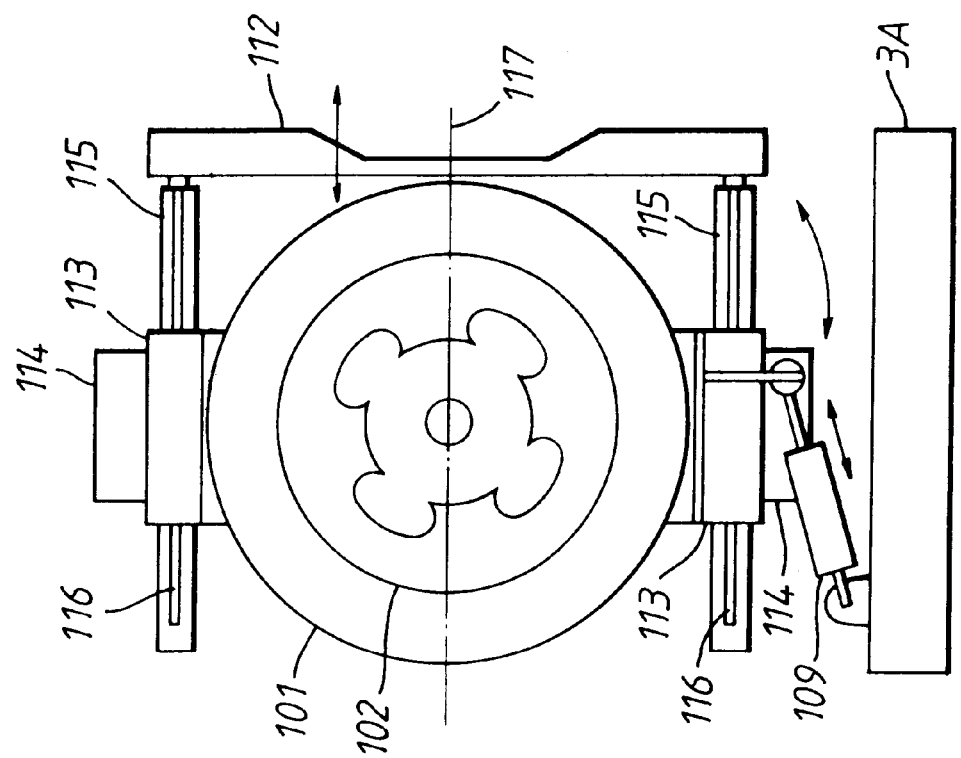
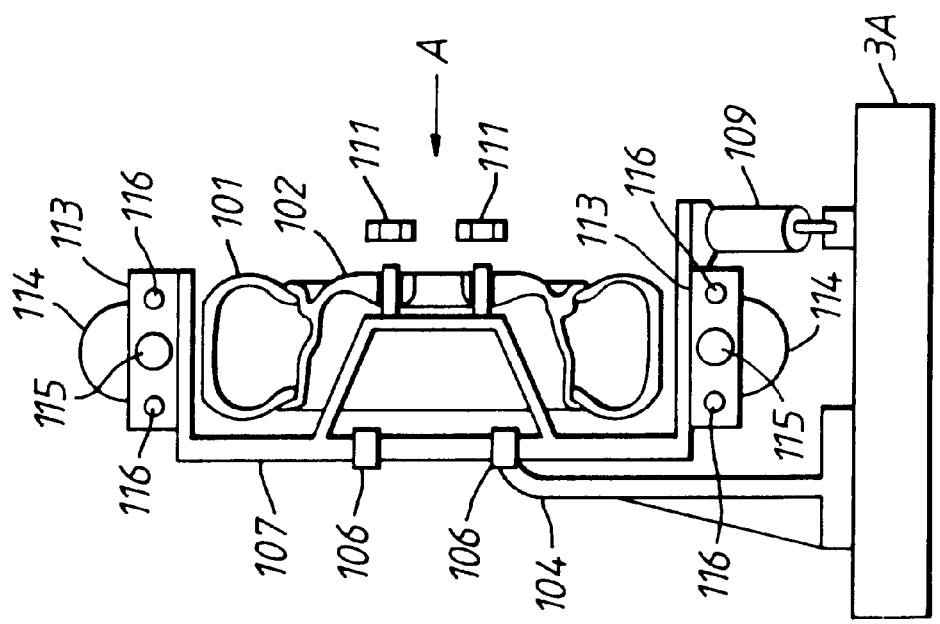
Fig. 7 (b)
Fig. 7 (a)

5,917,876

COMPUTED TOMOGRAPHY SCANNER

This application is a continuation of application Ser. No. 08/684,198, filed on Jul 19, 1996, now abandoned, which is a continuation of application Ser. No. 08/335,969, filed on Nov 4, 1994, abandoned.

BACKGROUND OF THE INVENTION

1. Field of the Invention

This invention relates to a computed tomography scanner that is adapted, for example, to non-destructive examination devices.

2. Description of the Related Art

Computed tomography scanners of this kind (hereinbelow abbreviated to CTs) include second-generation CTs of, for example, the traverse/rotation (hereinbelow abbreviated to T/R) system shown in FIG. 9 and third-generation CTs of the rotate/rotate system (hereinbelow abbreviated to R/R) shown in FIG. 10.

In a second-generation CT of the T/R system shown in FIG. 9, an X-ray fan beam 4 of fan angle $\alpha$ that is output from an X-ray source 1 is directed on to a subject to be examined not shown, placed on a T/R table 3 corresponding to the scanning area. Meanwhile, T/R table 3, on which the subject is placed, is rotated as shown by an arrow R and is traversed as shown by an arrow T, thereby effecting scanning. The X-rays that have passed through the subject are detected by a detector 2. This X-ray transmission data of the subject that is thus detected is collected, and this collected X-ray transmission data of the subject is subjected to processing by a reconstruction device, not shown, to obtain a tomographic image of the subject. With T/R table 3, the necessary scanning area is guaranteed by the space between X-ray source 1 and detector 2. From the point of view of efficiency of utilization of the X-rays, a distance SDD between X-ray source 1 and detector 2 should be very small.

Hereinafter scanning will be described in more detail. A prescribed distance traverse operation as shown by arrow T in FIG. 9 is performed such that T/R table 3 is made to traverse through the fan angle $\alpha$ of the X-ray beam. Indexing of the angle of rotation of T/R table 3 is performed with fan angle $\alpha$, and data collection is performed by effecting rotation through an angle $\alpha$ for each traverse.

The prior art second-generation CT of the T/R system described above is disclosed in detail in U.S. Pat. No. 5,027,378 issued on Jun 25, 1991.

However, when a subject is placed on T/R table 3, if some parts of the subject stick out from T/R table 3, they interfere with, for example, the X-ray shutter, the collimator and the frame etc, not shown, on X-ray source 1 side, or interfere with structural objects, not shown, on detector 2 side, with the result that scanning cannot be achieved. In general, T/R table 3 would be capable of 360° rotation.

In the case of the third-generation CT of the R/R system shown in FIG. 10, the arrangement of X-ray source 1 and detector 2 is the same as in FIG. 9. In this system, instead of both traverse and rotation only rotation can be performed, and the scanning action is achieved solely by rotation of a R table 5, by rotating R table 5 as shown by arrow R.

Also, when a subject is placed on R table 5, just as in the case of the T/R system described above, if the subject is placed on R table 5 with some parts sticking out, such parts of the subject interfere with structural items, not shown around the periphery of X-ray source 1 or detector 2, preventing scanning. Also, in general, R table 5 can be rotated through 360°.

As described above, in the case of the prior art CTs as shown in FIG. 9 and FIG. 10, if the subject has external dimensions larger than the scanning area, there is the problem that scanning cannot be achieved.

SUMMARY OF THE INVENTION

Accordingly, one object of this invention is to provide a computed tomography scanner which can achieve CT scanning and can obtain a tomographic image of a subject to be examined even when parts of the subject project beyond the scanning area.

Another object of this invention is to provide a computed tomography scanner in which the distance between the radiation emitting device and the radiation detecting device can be made smaller, and which can raise the radiation utilization efficiency and can be reduced in size and weight.

Still another object of this invention is to provide a computed tomography scanner which can scan only a specified part of a subject to be examined and can thereby obtain a tomographic image of increased spatial resolution and SN ratio.

These and other objects of this invention can be achieved by providing a computed tomography scanner for obtaining a tomographic image of a subject to be examined including a radiation emitting device for emitting radiation in a shape of a fan beam to the subject, a radiation detecting device for detecting the radiation that has passed through the subject to obtain detection data with respect to a tomographic plane of the subject. The radiation emitting device and the radiation detecting device determines a scanning area constituting a data collection region in a radiation plane of the fan beam. The subject has external dimensions exceeding the scanning area. The computed tomography scanner further includes a scanning device for relatively moving the subject, the radiation emitting device and the radiation detecting device in a condition that the radiation plane and the tomographic plane are on a same plane and a device for obtaining the tomographic image of a part of the subject corresponding to the scanning area from the detection data obtained by the radiation detecting device.

With a computed tomography scanner of this invention, a subject that projects outside the scanning area can be arranged on one side only towards the radiation detection device side or radiation emitting device side. For data collection, scanning is carried out such that the rotation is (180°−fan angle $\alpha$) in the case of the traverse/rotation system or (180°+fan angle $\alpha$) in the case of the rotate/rotate system, and a reciprocating rotary action can be performed that is symmetric with respect to the line joining the centers of the radiation emitting device and radiation detecting device.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 7 is a view showing the detailed layout of the mechanical unit of the embodiment illustrated in FIG. 1;

DETAILED DESCRIPTION OF THE PREFERRED EMBODIMENTS

Figure 1:
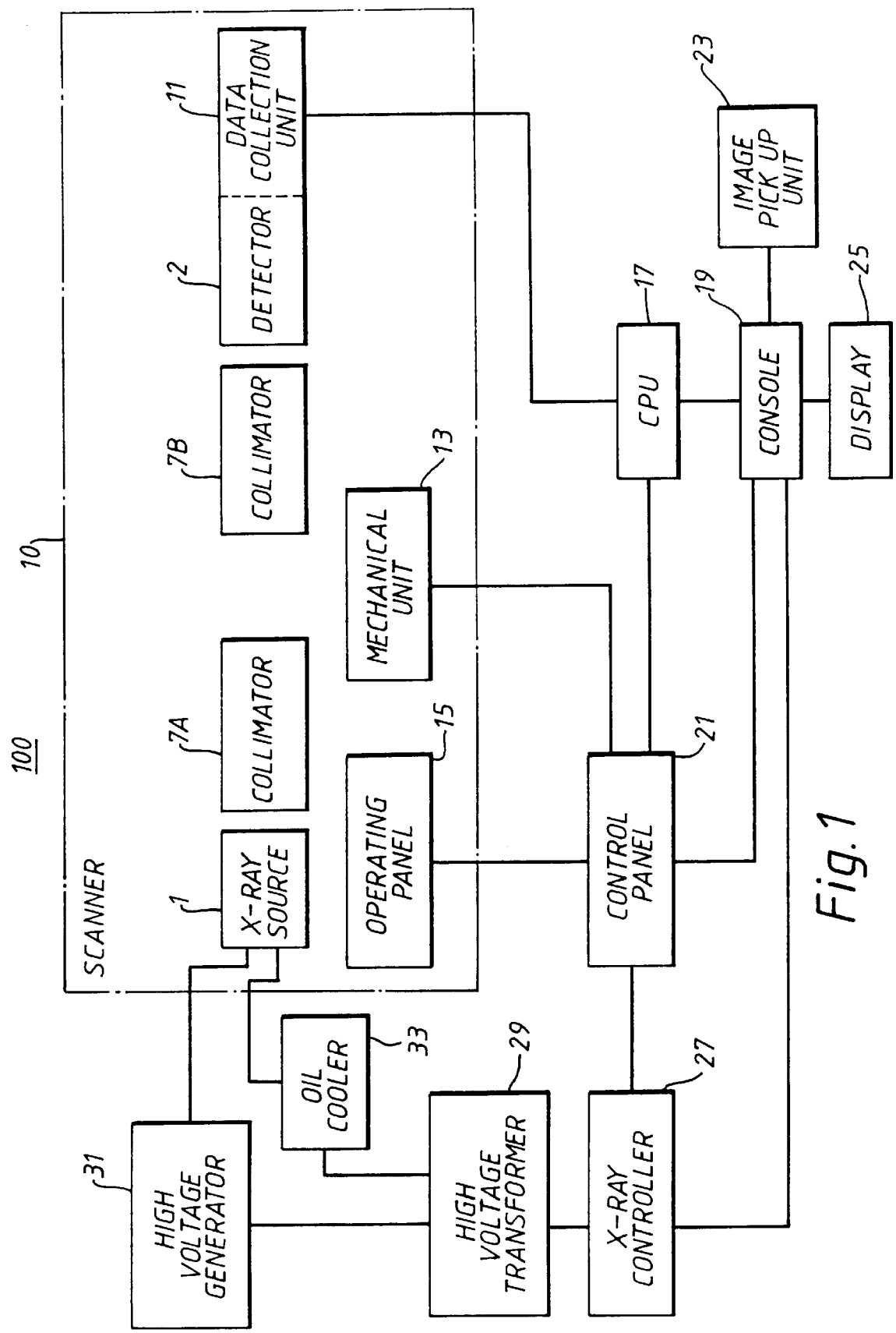
FIG. 1 is a block diagram illustrating the layout of a computed tomography scanner according to an embodiment of this invention.

Referring now to the drawings, wherein like reference numerals designate identical or corresponding parts throughout the several views, the embodiments of this invention will be described below.

FIG. 1 is a block diagram illustrating the layout of a computed tomography scanner 100 according to an embodiment of this invention. In this Figure, a scanner 10 is composed of X-ray source 1 consisting of an X-ray tube that continuously emits X-rays, a collimator 7A that shapes the X-rays emitted from this X-ray source 1 to a fixed fan beam shape, a collimator 7B that prevents incidence of the X-rays outside the prescribed directions, detector 2 that detects X-rays that have passed through the subject, and a data collection unit 11 that executes processing such as A/D conversion on the detection data output from detector 2 and outputs as projection data. Furthermore, scanner 10 includes a mechanical unit 13 which is provided with, in the case of the T/R system, a traverse mechanism and rotation mechanism, or, in the case of the R/R system, a rotation mechanism etc, and an operating panel 15 for inputting the settings of various measurement conditions etc.

Also, detector 2 is composed of, for example, a combination of 22 detection blocks each constituted by 8 photodiodes and 8 scintillators respectively, thereby providing 176 channels (8 channels per block). In the case of the R/R system, there would be at least 512 channels in detector 2.

A CPU 17 is connected to scanner 10, a console 19 and a control panel 21. CPU 17 controls the operation of computed tomography scanner 100 as a whole, and reconstructs a tomographic image of the subject whilst applying various kinds of correction, using the projection data that are input from data collection unit 11.

Console 19 is used to control the execution of various operations, and is connected to an image pickup unit 23, display 25 and X-ray controller 27.

Display 25 displays the setting conditions etc that are input from operating panel 15 and also displays a tomographic image of the subject that is reconstructed by CPU 17.

Image pick-up unit 23 picks up and records the tomographic image that is displayed on display 25 under the control of CPU 17 through console 19.

Control panel 21 is connected to mechanical unit 13, operating panel 15, CPU 17, console 19, and X-ray controller 27. Control panel 21 controls mechanical unit 13 and X-ray controller 27 in accordance with control instruction from CPU 17 or operating instructions from operating panel 15 and console 19. X-ray controller 27 controls the voltage and current of X-ray tube.

A high voltage transformer 29 together with a high voltage generator 31 generates high voltage drive power, which is supplied to X-ray source 1. An oil cooler 33 cools X-ray source 1 and high voltage transformer 29.

Figure 2:
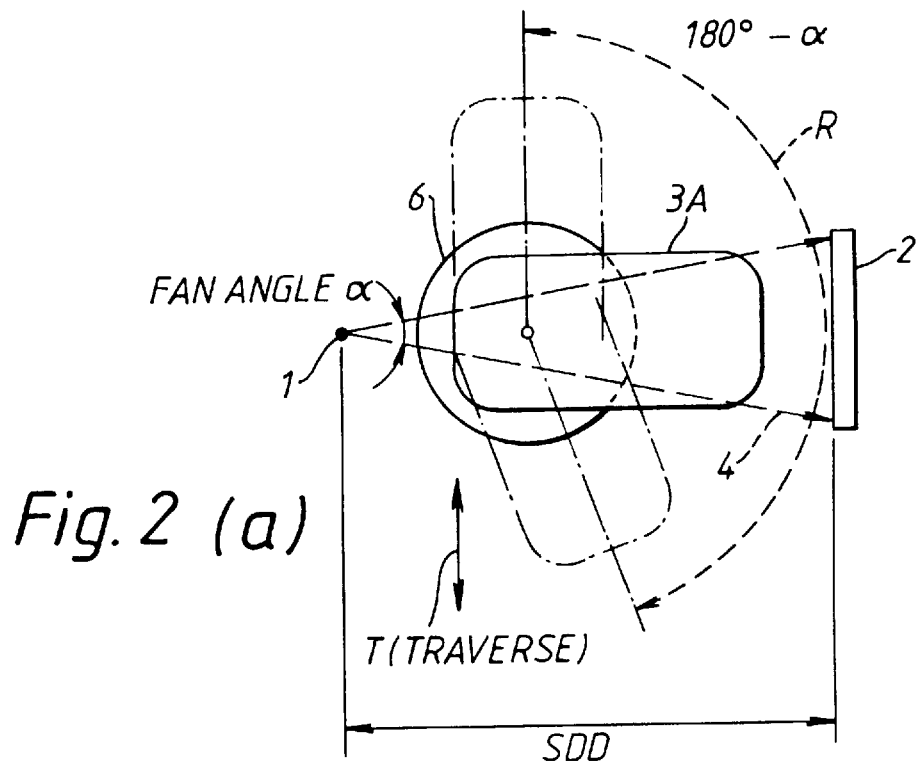
FIG. 2 is an explanatory diagram of the X-ray geometry of a second-generation CT of the T-R system according to an embodiment of this invention.
Figure 2:
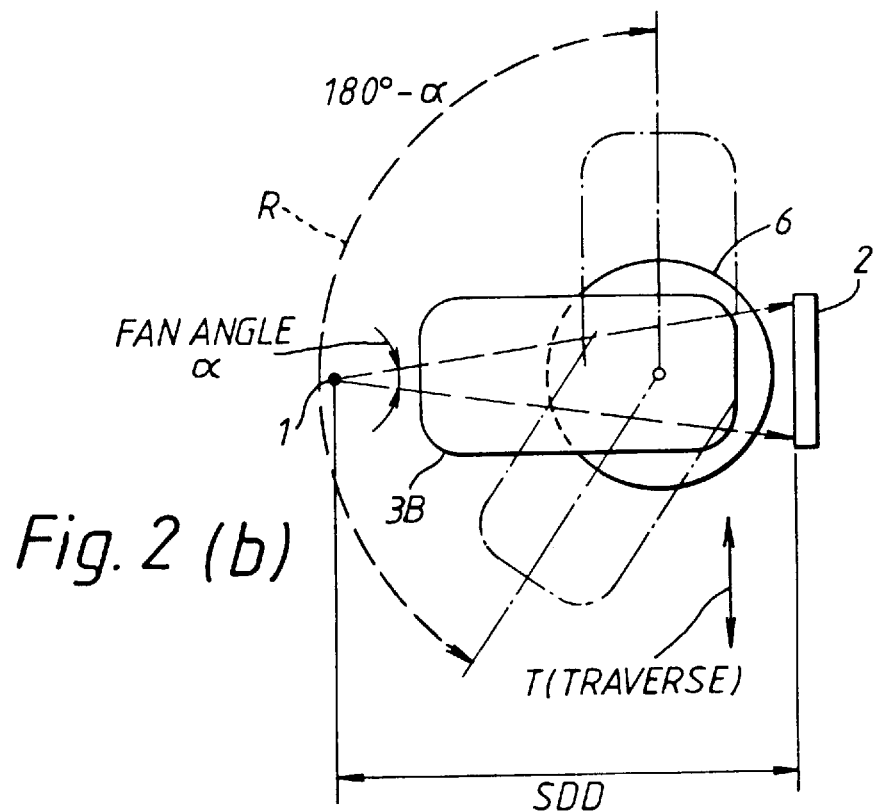

FIG. 2 is a diagram illustrating the X-ray geometric system and scanning system of the second generation CT of the T/R system. In FIG. 2(a), scanning area 6 is formed on the side near X-ray source 1 with respect to X-ray fan beam 4 determined by X-ray source 1 and detector 2, and T/R table 3A is provided, being of a shape which projects from scanning area 6 towards detector 2. In FIG. 2(b), scanning area 6 is formed on the side near detector 2, and T/R table 3B is arranged so as to project towards X-ray source 1 from scanning area 6. Also, in these case, traversing is performed in the direction as shown by arrow T, and rotation is performed through (180°−α), as shown by arrow R.

T/R systems shown in FIGS. 2(a) and (b) can be employed in the embodiment of this invention shown in FIG. 1.

Figure 3:
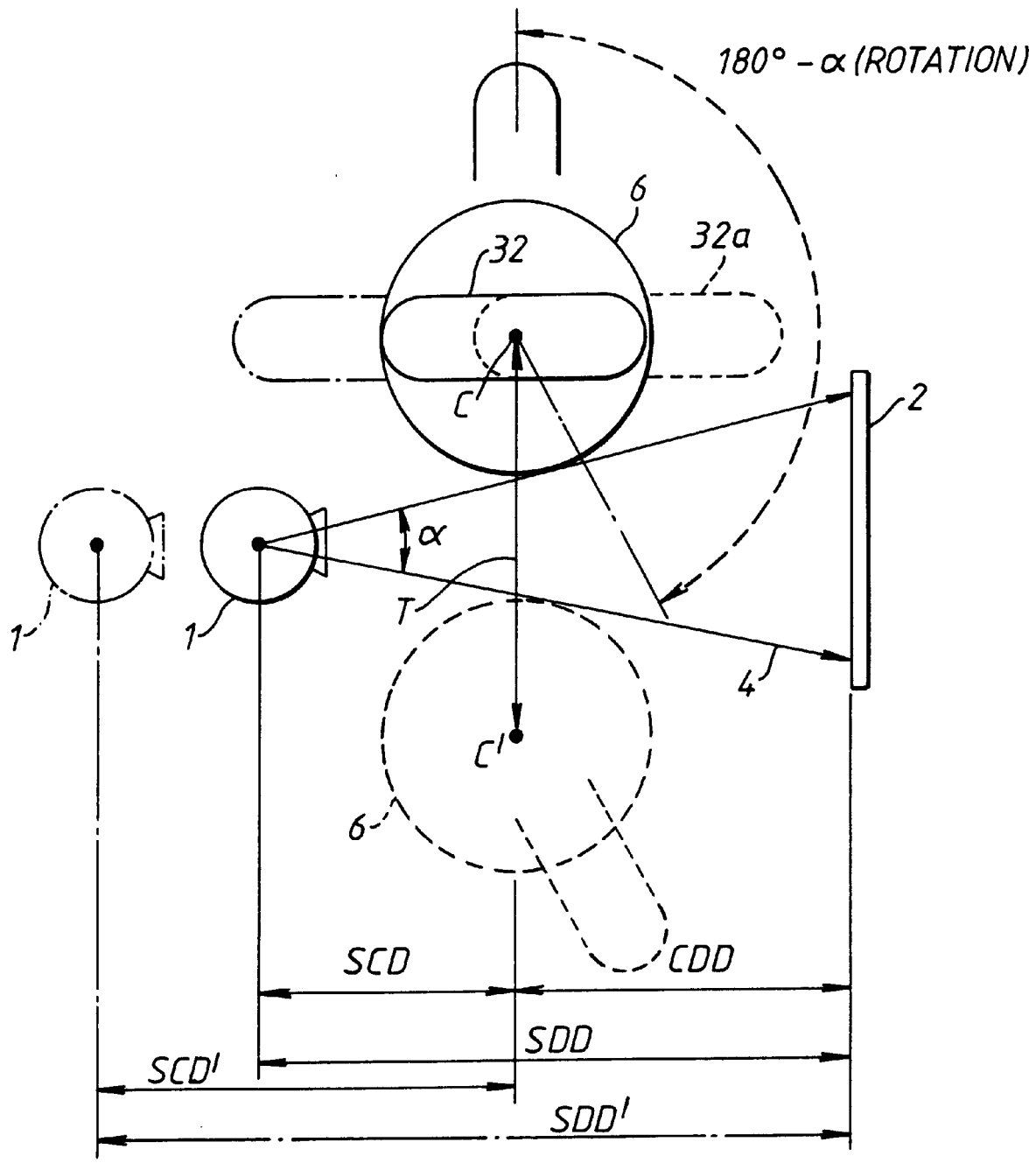
FIG. 3 is an explanatory diagram of the X-ray geometry of a second-generation CT of the T-R system.

FIG. 3 shows the X-ray geometry and scanning system of a second-generation CT which is also of the T/R system, like FIG. 2(a). Scanning area 6 is likewise arranged on the side near X-ray source 1 with respect to X-ray fan beam 4 determined by X-ray source 1 and detector 2, and T/R table 32 is arranged within scanning area 6. In this case also, just as in the case of FIG. 2 (a), traversing as shown by arrow T and rotation are performed, and rotation is likewise through (180°−α). Next, the cases are considered in which T/R table 32 projects towards detector 2, as shown by the dotted line 32a. In a first case in which rotation is performed within the range (180°−α), as shown in FIG. 3, projecting portion 32a of T/R table 32 does not collide with X-ray source 1, so that distance SDD between X-ray source 1 and detector 2 is comparatively shorter, as shown. But in a second case in which T/R table 32 rotates through 360° as shown by the double-dashed lines, the required distance between X-ray source 1 and detector 2 becomes SDD' as shown in the drawings. Consequently, when T/R table 32 projects towards detector 2 as shown by 32a, distance SDD in the first case becomes smaller than distance SDD' in the second case of 360 degree rotation by the difference between distances SCD and SCD' of X-ray sources 1 and center C of scanning area 6, through a distance CDD between center C of scanning area 6 and detector 2 is not changed in the two cases.

As described in FIG. 3, in the case of FIGS. 2(a) or (b), the distance SDD between X-ray source 1 and detector 2 can be reduced, enabling the overall equipment size to be reduced, by having T/R table 3A or 3B offset towards X-ray source 1 or detector 2 and having it projected on the opposite side, and performing rotation through (180°−α). It should be noted that data collection can still be performed without violating the requirements of CT projection data by performing rotation with an Angle of (180°−α) during scanning.

Figure 4:
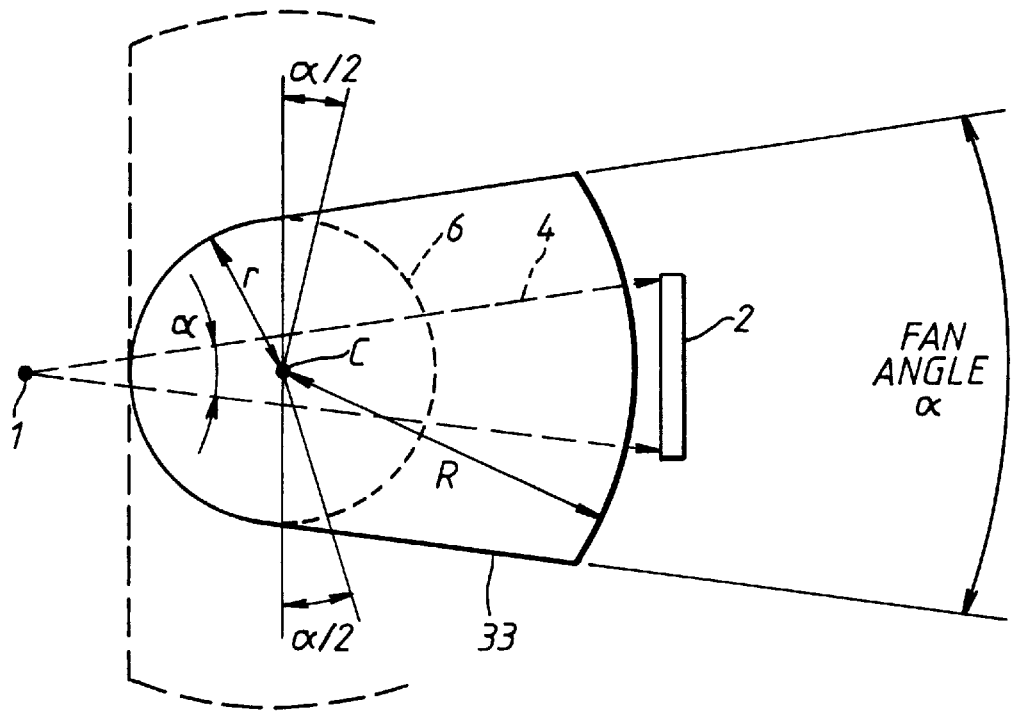
FIG. 4 is an explanatory diagram of the X-ray geometry of a second-generation CT of the T-R system according to an embodiment of this invention.

FIG. 4 is a view showing the X-ray geometry of a second generation CT of the T/R system. In this Figure, a T/R table 33 is provided that projects towards detector 2 from scanning area 6 with respect to X-ray fan beam 4 determined by X-ray source 1 and detector 2. The arc portion near X-ray source 1 of T/R table 33 coincides with scanning area 6 and its radius is r. The radius from the center C of scanning area 6 of the part of T/R table 33 projecting towards detector 2 is R.

T/R table 33 shown in FIG. 4 can be used in mechanical unit 13 of the embodiment shown in FIG. 1.

Figure 5:
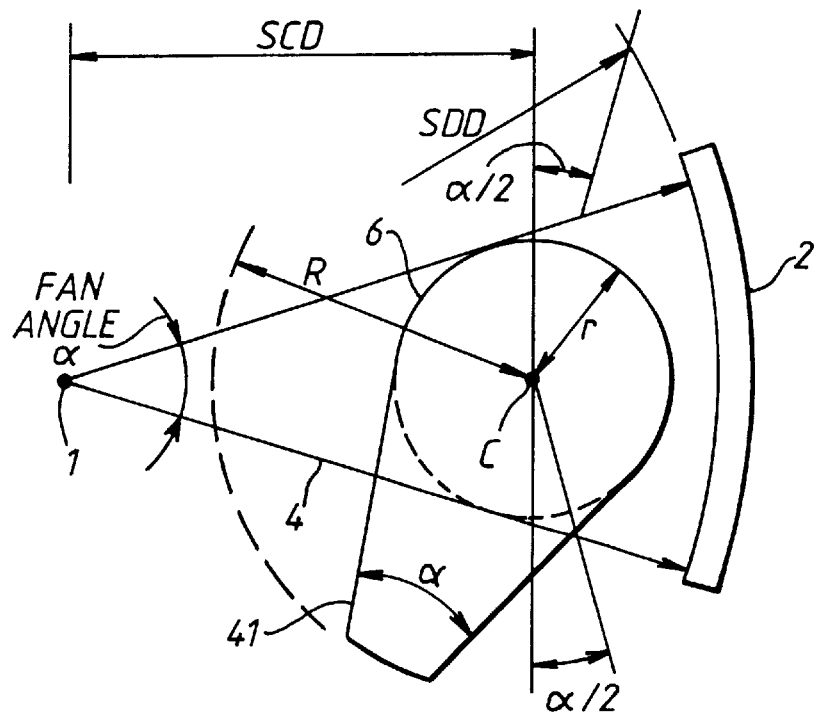
FIG. 5 is an explanatory diagram of the X-ray geometry of a third-generation CT of the R—R system according to an embodiment of this invention.

FIG. 5 shows the X-ray geometry of a third generation CT of the R/R system. In this Figure, scanning area 6 is positioned near to detector 2 within X-ray fan beam 4 determined by X-ray source 1 and detector 2. Table 41 is arranged having a portion that projects with fan angle α, the same as fan beam 4, towards X-ray source 1 from scanning area 6.

In the case of a CT of the R/R system, as shown in FIG. 5, fan angle α must provide an angle sufficient to cover scanning area 6. In general, because of restriction on the X-ray emission angle of the X-ray source 1, distance SCD between X-ray source 1 and center C of scanning area 6 is large. On account of this, as shown in FIG. 5, the case of projection of table 41 towards X-ray source 1 enables distance SDD between X-ray source 1 and detector 2 to be made smaller than in the case of projection towards detector 2.

The tomographic plane can be reconstructed by picking up the projection data within the angular range (180°+α). Of course, in the case of an X-ray source 1 whose fan angle α can be taken larger, an arrangement can be adopted in which projection is allowed towards detector 2.

In FIG. 5, the radius of the portion of scanning area 6 constituted by table 41 is r, and the radius of the portion projecting towards X-ray source 1 from this portion is R, as shown.

Table 41 shown in FIG. 5 can also be used in mechanical unit 13 of the embodiment shown in FIG. 1.

FIG. 4 and FIG. 5 show the boundaries of the table shape determined from the X-ray geometry. The various restricting conditions may be summarized as follows in table 1.

TABLE 1

| Scanning system | r | R | Extension of table |
| --- | --- | --- | --- |
| T/R (Fig. 4) | Scanning area | Distance from Scanning center to structural item | Wider area in which scanning area is enclosed by α |
| R/R (Fig. 5) | As above | As above | Narrower area in which scanning area is enclosed by α |

The difference between the extents of the tables in the T/R system and R/R system is determined by the angle (180°±α) through which the table can rotate in the scanning system in question. Also reciprocatory operation is performed within the range of rotation through angle (180°±α).

Figure 6:
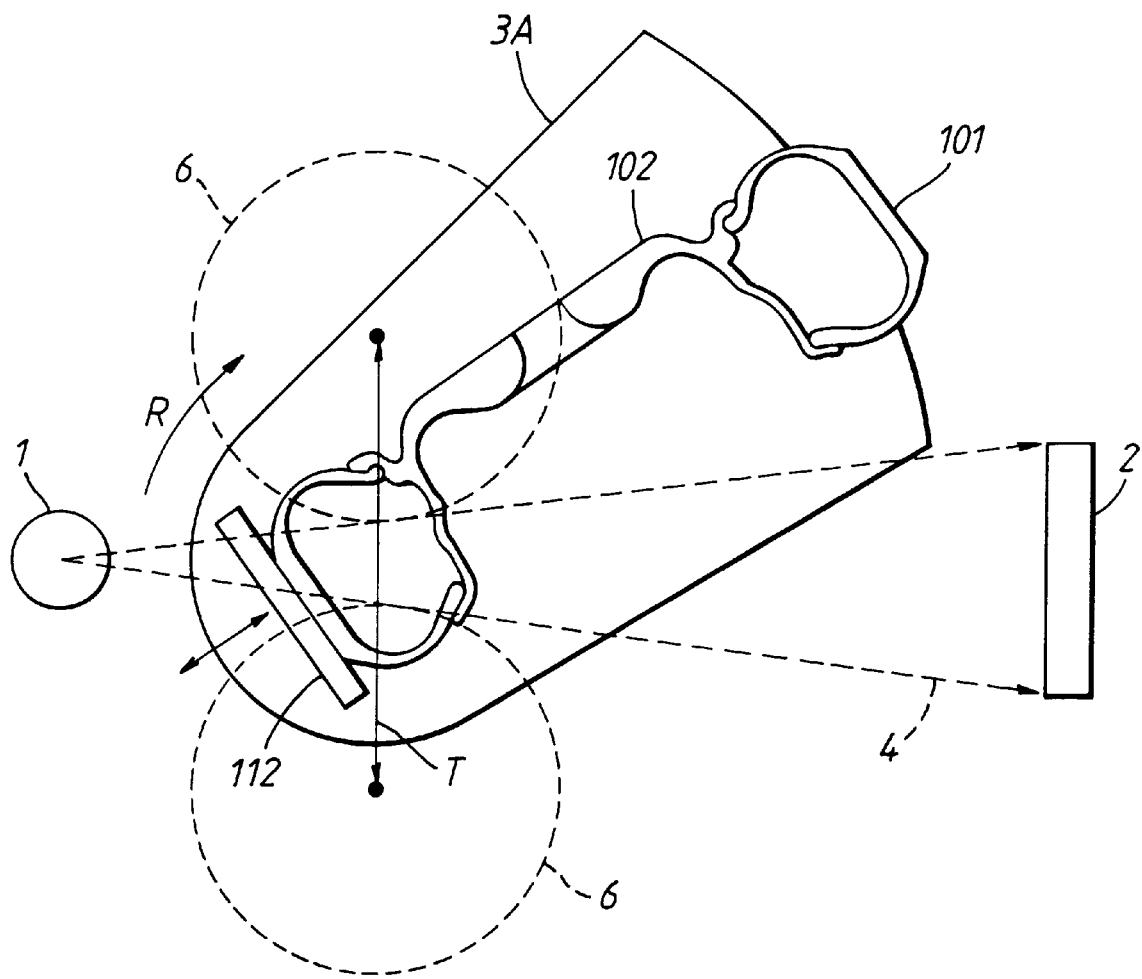
FIG. 6 is a view showing the X-ray geometry of the embodiment with the mechanical unit illustrated in FIG. 7.

Hereinbelow mechanical unit 13 of the embodiment shown in FIG. 1 will be described in detail. FIG. 7 is a view showing the detailed layout of mechanical unit 13 of the embodiment illustrated in FIG. 1. FIG. 6 is a view showing the X-ray geometry of the embodiment with mechanical unit 13 shown in FIG. 7. Mechanical unit 13 shown in FIG. 6 and FIG. 7 is adapted to a CT for tires which images a tomographic plane of one side of a tire, as an example. The tomographic plane on one side of the tire is arranged to be imaged by an arrangement with the same geometry as FIG. 2(a). FIG. 7(b) is a view seen from the direction of arrow A in FIG. 7(a). FIG. 6 shows the X-ray geometry at a tomographic plane 117 shown in FIG. 7(b).

In FIG. 6 and FIG. 7, a tires 101 is supported by a wheel 102 and the load is applied to tires 101 by a loading plate 112. FIGS. 7(a) and (b) show how the load is applied to tyre 101. A support base 104 is fixed on a T/R table 3A that constitutes the scanning means capable of traverse/rotation. T/R table 3A is provided with traverse function provided by a rail and traverse mechanism etc. and rotation function. Support base 104 is provided with a holder 107 which is rotatable and constitutes tires support means, through a rotary support unit 106 constituted by a bearing. A rotary drive unit 109 is provided between the bottom end of holder 107 and T/R table 3A. Holder 107 is arranged to be rotated by extension and contraction of rotary drive unit 109 by a control signal from control panel 21. The subject, constituted by tires 101, is mounted on ordinary commercial wheel 102 and is maintained in holder 107 by means of screws 111 at the hub portion of this wheel 102.

Above and below holder 107 there are provided drive means for pressing a pressure plate or load plate 112 constituting load means against tires 101. Drive means is composed of a drive unit 113, a drive screw rod 115, a support shaft 116 and a drive motor 114. By means of this mechanism, load plate 112 can be moved in the left or right direction of FIG. 7(b). Also, as described above, X-ray source 1 and detector 2 are arranged opposite each other in positions on either side of tires 101 supported on holder 107.

The tomographic plane 117 that is scanned by the X-rays on the fan beam that is emitted from X-ray source 1 is usually formed as shown in FIG. 7(b) on a plane passing through the wheel center, which is also the center of tires 101. A pressure measurement device, not shown, is provided on the pressurizing mechanism including load plate 112 so that the load force or pressurizing force can be suitably regulated.

In the CT for tires constructed as above, in non-destructive inspection of tires 101, tires 101 is first mounted on holder 107 by the hub portion of wheel 102. Then, tires 101 is rotated and held by rotary drive unit 109 such that the tomographic plane 117 of the desired tomographic image coincides with the plane of the X-ray fan beam that is emitted by X-ray source 1. In this condition, load plate 112 is driven by drive unit 113 so that a suitable load is applied to tires 101. After this, a prescribed distance traverse operation as shown by arrow T in FIG. 6 is performed such that T/R table 3A is made to traverse through the fan angle α of the X-ray beam. Indexing of the angle of rotation of T/R table 3A is performed with fan angle α, and data collection is performed by effecting rotation through an angle α for each traverse.

As described above, with this embodiment, a tomographic image can be obtained in a condition in which load is applied to tire 101. X-ray source 1 does not need to be inserted into the hollow space of tires 101 as it would with a conventional CT for tires. An ordinary commercial wheel 102 can therefore be used without modification. Tires 101 can be mounted from A direction in FIG. 7(a) by using holder 107, so convenient operation can be achieved. Since there are provided rotary holding unit 106 of tires 101 and rotary drive unit 109 of tires 101, the scanning position i.e. the position of the tomographic plane can easily be altered. Consequently, a tomographic image can be obtained with respect to the portions of tires 101 from the road-contacting region of tire 101 to the raised portions of the tires tread.

Combination with mechanical tests of the tires enables various load tests of tires braking, steering, side walls and bead in addition to the test described above. Also, CT scanning can be performed under other experimental conditions, not just under a condition with load applied to tires 101 by a load plate as described above.

As described above, with this embodiment, scanning can be performed of a part of a subject to be examined that projects beyond the scanning area. Also, compared with a CT that scans the entire subject to be scanned, distance SDD between X-ray source 1 and detector 2 can be made smaller, and the X-ray utilization efficiency can be raised. Also, the computed tomography scanner as a whole can be reduced in size and in weight.

Since distance SDD between X-ray source 1 and detector 2 can be made small, the number of channels of detector 2 can be reduced, enabling detector 2 to be made of smaller size. As shown in FIGS. 2(a) and 3, the distance between X-ray source 1 and scanning area 6 can be made small, so, if the dimensions of the X-ray focal spot are small, the spatial resolution can be raised. Also, the traverse distance can be shortened, enabling the computed tomography scanner as a whole to be reduced in size and weight. As scanning of a part of a subject is possible, spatial resolution and/or image SN ratio can be improved.

In the embodiment shown in FIG. 6 and FIG. 7, CT scanning can be performed in a condition in which air pressure is applied to the tires and in a condition with load applied to the tires. Also, scanning can be performed whilst conducting other mechanical tests. Furthermore, in a CT for tire, scanning can be reduced to the portion of the tyre under test. So, the traverse distance can be shortened and scanning area 6 will be nearer to the X-ray focal spot, thereby enabling a tomographic image of increased spatial resolution and SN ratio.

It should be noted that, although, in the above embodiments, second generation and third generation CTs were described, the same benefits can be obtained with CTs using other scanning systems by taking into consideration fan angel α and data collection range. Also, the same benefits can be obtained with other types of radiation source and detector, not just X-rays.

The scanning area can be altered, in the case of the T/R system, by altering the traverse distance and data sampling pitch etc, or, in the case of the R/R system, by shifting the center of rotation between the X-ray source and the detector.

Figure 8:
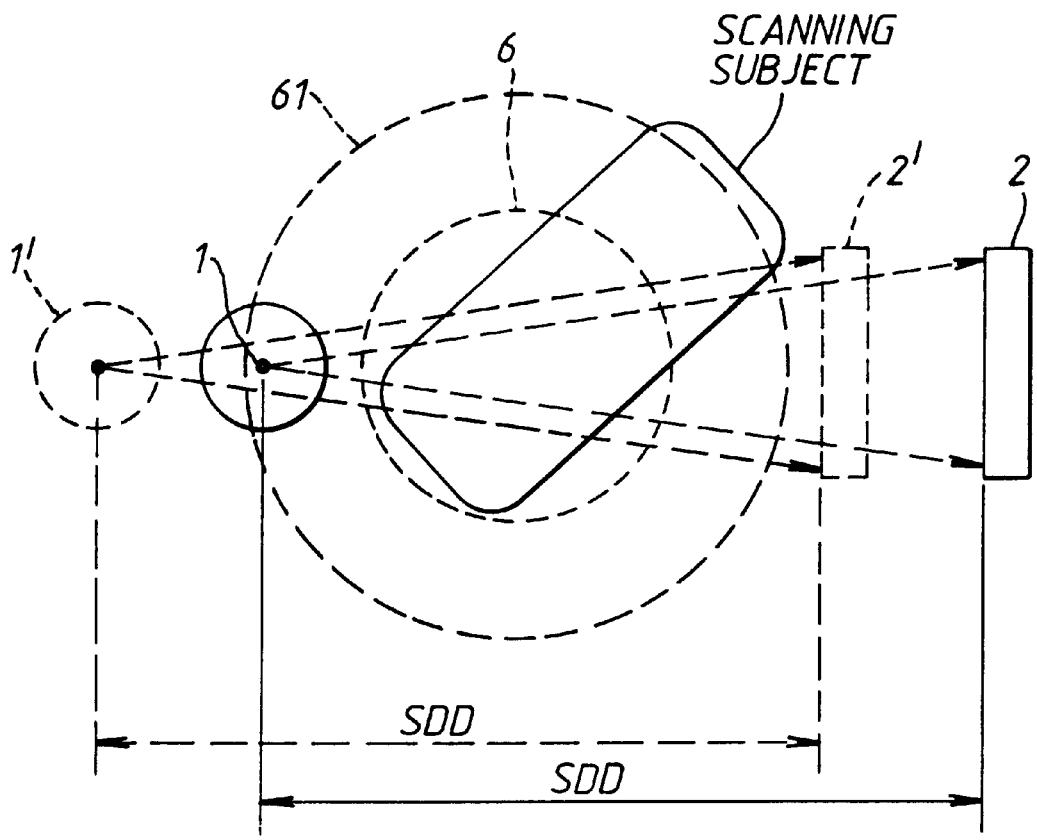
FIG. 8 is a diagram illustrating a method of varying the scanning area in a T/R system according to another embodiment of this invention.
Figure 9:
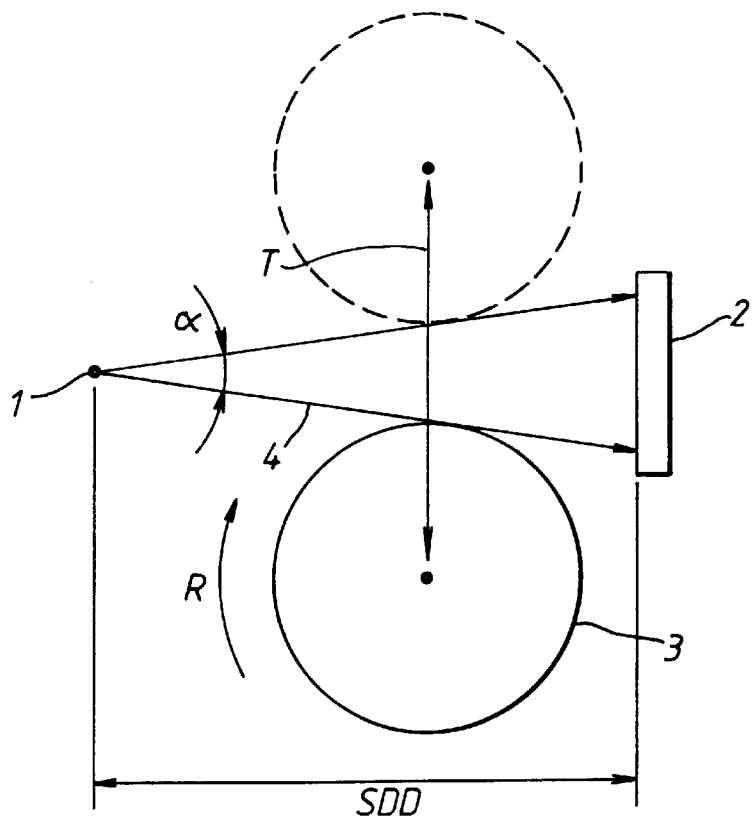
FIG. 9 is a view illustrating a prior art example of a second-generation CT of the T/R system.
Figure 10:
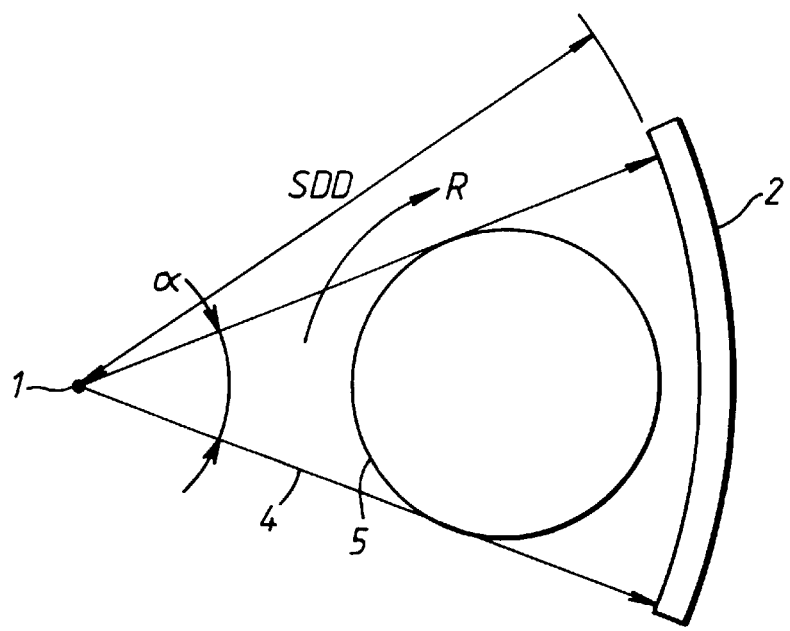
FIG. 10 is a view illustrating a prior art example of a third-generation CT of the R/R system.

FIG. 8 is a diagram given in explanation of a method of varying the scanning area of the T/R system. X-ray source 1 and detector 2 are shifted to positions 1', 2' as shown by the dotted lines, whilst maintaining distance SDD between X-ray source 1 and detector 2 constant. By this shifting scanning area 6 is made much wider as shown by 61, since the space wherein there is no interference with the subject of scanning can be widened.

Also, the same effect can be obtained by fixing X-ray source 1 and detector 2 and shifting the traverse position of the T/R table in the left or right direction.

In the alteration of the scanning area described above, the scanning area was varied with the geometry between X-ray source 1 and detector 2 kept fixed. However it is also possible to move X-ray source 1 and detector 2 with respect to the center of scanning so as to vary the geometry by changing the distance SDD between X-ray source 1 and detector 2. If this is done, the path (angle) of incidence of X-rays onto detector 2 from the X-ray source will change, so separators between the channels of detector 2 or countermeasures to prevent cross-talk must be fully considered.

As described above, with this invention, the subject to be examined can be arranged sticking out from the scanning area towards one only of the radiation detecting device or radiation emitting device, so a partial tomographic image can be obtained even from a subject whose external dimensions are larger than the scanning area. Also, the distance between the radiation emitting device and radiation detecting device can be made smaller, so the radiation utilization efficiency can be raised and the computed tomography scanner as a whole can be reduced in size and weight.

Furthermore, as scanning of a specified part of a subject is possible, spatial resolution and/or image SN ratio can be improved.

Obviously, numerous modifications and variations of the present invention are possible in light of the above teachings. It is therefore to be understood that within the scope of the appended claims, the invention may be practiced otherwise than as specifically described herein.

What is claimed is:

1. A computed tomography scanner for examining a tire or wheel using penetrating radiation, comprising:

a radiation source configured to emit, in a predetermined fan plane, a fan beam of radiation, forming a predetermined fan angle α;

a holder configured to support the tire or wheel so that a tomographic plane of the tire or wheel coincides with the predetermined fan plane, wherein the tomographic plane is substantially parallel to the tire or wheel's rotational axis and an intersection thereof with the tire or wheel defines first and second cross-sections and wherein a scan area is predetermined on the tomographic plane as an area including the first cross-section and excluding the second cross-section;

a radiation detector, geometrically fixed to the radiation source and together therewith forming a measuring system, configured to detect, with a spatial resolution, the radiation after passage through the first cross-section within the fan angle α, and configured to provide output signals based on radiation absorption by the tire or wheel; and a rotation device configured to rotate the holder or the measuring system with respect to each other around an axis passing through a center of the scan area and normal to the predetermined fan plane;

wherein the measuring system is geometrically fixed to the holder such that the scan area is maintained closer to one of:

the radiation source, so that a rotation range of the rotation device is limited such that a direction of rotation of the second cross-section about the scan area comprises an angular range of at least (180−α)°, and so that the second cross-section does not interfere with the radiation detector during rotation, and the radiation detector, so that a rotation range of the rotation device is limited such that a direction of rotation of the second cross-section about the scan area comprises an angular range of at least (180−α)°, and so that the second cross-section does not interfere with the radiation source during rotation.

2. The computed tomography scanner of claim 1, further comprising:

a pressurizing device configured to maintain the tire at a predetermined pressurized state.

3. The computed tomography scanner of claim 2, further comprising:

a pressure plate configured to apply a predetermined load to the tire while the tire is in the predetermined pressurized state.

4. The computed tomography scanner of claim 3, further comprising:

a traverse device configured to traverse the holder or the measuring system with respect to each other along the predetermined fan plane in a direction normal to a central line of the fan angle α, in a traverse range sufficiently large so that the scan area completely traverses the fan angle α.

5. The computed tomography scanner of claim 4, further comprising:

a mechanical controller configured to control the traverse device and the rotation device and for alternately performing sequential motion of traverse and rotation in a step angle equal to the fan angle α at least (180°/α) times of the traverses and at least (180°/α1) times of the rotations.

6. The computed tomography scanner of claim 5, further comprising:

a data acquisition device configured to collect the output signals of the radiation detector during the traverse, to convert the output signals to digital data, and to generate a data set related to absorption of dense directions covering 180° of dense parallel paths covering the scan area.

7. The computed tomography scanner of claim 6, further comprising:

a data processor configured to reconstruct from the data set a tomographic image of a portion of the tire or wheel disposed in the scan area.

8. A computed tomography scanner for examining a tire or wheel using penetrating radiation, comprising:

a radiation source configured to emit, in a predetermined fan plane, a fan beam of radiation, forming a predetermined fan angle α;

a holder configured to support the tire or wheel so that a tomographic plane of the tire or wheel coincides with the predetermined fan plane, wherein the tomographic plane is substantially parallel to the tire or wheel's rotational axis and an intersection thereof with the tire or wheel defines first and second cross-sections and wherein a scan area is predetermined on the tomographic plane as an area including the first cross-section and excluding the second cross-section;

a radiation detector, geometrically fixed to the radiation source and together therewith forming a measuring system, configured to detect, with a spatial resolution, the radiation after passage through the first cross-section within the fan angle α, and configured to provide output signals based on radiation absorption by the tire or wheel; and a rotation device configured to rotate the holder or the measuring system with respect to each other around an axis passing through a center of the scan area and normal to the predetermined fan plane;

wherein the measuring system is geometrically fixed to the holder such that the scan area is maintained closer to one of:

the radiation source, so that a rotation range of the rotation device is limited such that a direction of rotation of the second cross-section about the scan area comprises an angular range of at least (180+α)°, and so that the second cross-section does not interfere with the radiation detector during rotation, and the radiation detector, so that a rotation range of the rotation device is limited such that a direction of rotation of the second cross-section about the scan area comprises an angular range of at least (180+α)°, and so that the second cross-section does not interfere with the radiation source during rotation.

9. The computed tomography scanner of claim 8, further comprising:

a pressurizing device configured to maintain the tire or wheel at a predetermined pressurized state.

10. The computed tomography of claim 8, further comprising:

a pressure plate configured to apply a predetermined load to the tire or wheel while the tire or wheel is in the predetermined pressurized state.

* * * * *